(12) United States Patent
Jacoby (10) Patent No.: US 9,788,922 B2
(45) Date of Patent: Oct. 17, 2017

(54) SYSTEMS AND METHODS FOR REMOVAL OF DENTAL BIOFILM USING IRRIGATION

(71) Applicant: Bennett H. Jacoby, Kona, HI (US)

(72) Inventor: Bennett H. Jacoby, Kona, HI (US)

( * ) Notice: Subject to any disclaimer, the term of this patent is extended or adjusted under 35 U.S.C. 154(b) by 62 days.

(21) Appl. No.: 14/681,716

(22) Filed: Apr. 8, 2015

(65) Prior Publication Data

US 2016/0296310 A1    Oct. 13, 2016

(51) Int. Cl.
*A61C 17/02* (2006.01)
*A61C 1/00* (2006.01)

(52) U.S. Cl.
CPC ...... *A61C 17/0211* (2013.01); *A61C 17/0208* (2013.01); *A61C 1/0061* (2013.01); *A61C 17/0217* (2013.01)

(58) Field of Classification Search
CPC ............ A61C 17/0211; A61C 17/0217; A61C 17/043; A61C 1/0061; A61C 1/0084; A61C 1/092
See application file for complete search history.

(56) References Cited

U.S. PATENT DOCUMENTS

| | | |
|---|---|---|
| 803,474 A | 10/1905 | Dennis |
| 1,500,107 A | 7/1924 | Chandler |
| 3,211,149 A | 10/1965 | Fono |
| 3,401,690 A | 9/1968 | Martin |
| 3,452,746 A | 7/1969 | Shanhouse |
| 3,481,329 A | 12/1969 | Warren, Jr. |
| 3,507,275 A | 4/1970 | Walker |
| 3,516,402 A | 6/1970 | Toth |
| 3,638,866 A | 2/1972 | Walker |
| 3,731,675 A | 5/1973 | Kelly |
| 3,742,942 A | 7/1973 | Westline |
| 3,756,225 A | 9/1973 | Moret et al. |
| 3,840,992 A | 10/1974 | English |
| 4,106,501 A | 8/1978 | Ozbey et al. |
| 4,237,574 A | 12/1980 | Kelly et al. |
| 4,560,351 A | 12/1985 | Osborne |
| 4,834,110 A | 5/1989 | Richard |

(Continued)

FOREIGN PATENT DOCUMENTS

| | | |
|---|---|---|
| EP | 0377594 A1 | 7/1990 |
| EP | 0865770 A1 | 9/1998 |

(Continued)

*Primary Examiner* — Paula J Stice
(74) *Attorney, Agent, or Firm* — Morriss O'Bryant Compagni (57) ABSTRACT

Systems and methods for cleaning teeth by removal of dental biofilm. In one illustrative embodiment, a custom fit tray that fits over the teeth and seals against the gum of a mammal. A number of ports are embedded in the tray, each in fluid communication with a hose or line supplied with either a vacuum or an irrigant/fluid source. A small space between the tray and the teeth provides for fluid to flow around the teeth. A router may be connected to both an irrigant fluid supply reservoir and a vacuum pump to direct either fluid or vacuum to the various hoses with the routing changing over time for optimum cleaning. Air may be injected into the cleaning fluid in varying amounts, to create bubbles, water droplets, and/or boluses of the cleaning fluid to increase and focus the hydrodynamic forces of the fluid upon reaching the teeth.

21 Claims, 5 Drawing Sheets

(56) References Cited

U.S. PATENT DOCUMENTS

| | | |
|---|---|---|
| 4,865,021 A | 9/1989 | Siderman |
| 4,991,570 A | 2/1991 | Bullard |
| 5,104,315 A | 4/1992 | McKinley |
| 5,513,986 A | 5/1996 | Feltham et al. |
| 5,573,398 A | 11/1996 | Towle et al. |
| 5,800,367 A | 9/1998 | Saxer et al. |
| 6,406,447 B1 | 6/2002 | Thrash et al. |
| 6,638,236 B2 | 10/2003 | Thrash et al. |
| 6,893,259 B1 | 5/2005 | Reizenson |
| 7,118,377 B2 | 10/2006 | Inoue et al. |
| 8,540,660 B2 | 9/2013 | Martin et al. |
| 8,617,090 B2 | 12/2013 | Fougere et al. |
| 8,684,956 B2 | 4/2014 | McDonough et al. |
| 9,504,542 B2 * | 11/2016 | De Gentile ........ A61C 17/0211 |
| 2010/0016908 A1 | 1/2010 | Martin et al. |
| 2011/0027746 A1 | 2/2011 | McDonough et al. |
| 2011/0027748 A1 | 2/2011 | Fusi, II et al. |
| 2011/0027758 A1 | 2/2011 | Ochs et al. |
| 2011/0065061 A1 | 3/2011 | Florman |
| 2011/0318705 A1 | 12/2011 | Sullivan et al. |
| 2012/0021375 A1 | 1/2012 | Binner et al. |
| 2012/0189976 A1 * | 7/2012 | McDonough ...... A61C 17/0202 433/89 |
| 2012/0199135 A1 * | 8/2012 | Podmore ................ A61F 5/566 128/848 |
| 2013/0081217 A1 | 4/2013 | Jeong |
| 2013/0236851 A1 | 9/2013 | McDonough et al. |
| 2014/0045140 A1 | 2/2014 | Soyama |
| 2016/0058526 A1 * | 3/2016 | Policicchio ............ A61C 3/025 433/29 |

FOREIGN PATENT DOCUMENTS

| | | |
|---|---|---|
| WO | 2004096078 A1 | 11/2004 |
| WO | 2010004264 A1 | 1/2010 |
| WO | 2014052778 A1 | 4/2014 |

* cited by examiner

SYSTEMS AND METHODS FOR REMOVAL OF DENTAL BIOFILM USING IRRIGATION

TECHNICAL FIELD

The present disclosure relates to methods and systems for cleaning teeth by removal of dental biofilm.

BACKGROUND

Periodontitis is one of the most common chronic diseases known to mammals, and humans in particular. It is estimated that 47.2% of adults aged 30 years and older have some form of periodontal disease. Periodontitis is caused by supragingival biofilm that promotes the formation of a subgingival biofilm which destroys the supporting bone and other supporting structures of the teeth, leading to chronic infection, systemic disease and tooth loss. This disease is treatable, but not curable, and usually reoccurs following treatment due to inadequate daily biofilm removal. If this biofilm were removed from all tooth surfaces or killed on a daily basis, then new and recurrent periodontitis could be eliminated.

Currently, dental biofilm can be adequately removed, but not killed, by thorough brushing and flossing, yet this is rarely if ever accomplished due to lack of patient or caretaker dexterity, compliance, and ability to assess the degree of biofilm removal.

Various chemical agents have been found to soften, dissolve and/or kill the bacterial biofilm (sodium hypochlorite solutions, povidone iodine solutions, chlorhexidine solutions, urea solutions, surfactants), but all of these agents are noxious and foul tasting such that patients tend to be non-compliant in their use.

Application of water with varied hydrodynamic parameters has been shown to partially remove biofilm and reduce gingival inflammation, but not to a level needed to completely control periodontitis. In addition, the devices developed to apply the water (such as the commercially available WATERPIK™ type devices) are patient directed without any ability for the patient to target all affected areas, therefore many areas are inadequately treated.

An automated system, device and method that was able to quickly, completely and consistently remove and/or kill clinically significant biofilm accumulation on the entire dentition on a daily basis would be an improvement in the art. Such a system or device that could be used directly by a patient on an automated basis would be a further improvement in the art.

SUMMARY

The present disclosure is directed to systems and methods for cleaning teeth by removal of dental biofilm to prevent or reduce dental disease. In one illustrative embodiment, a system in accordance with the present invention includes a custom fit tray that fits over the teeth and seals against the gum of a mammal. A number of ports are embedded in the tray, each in fluid communication with a hose or line. The hoses are supplied with either vacuum or an irrigant/fluid source. There is a small space between the tray and the teeth that provides for fluid to flow around the teeth.

In some embodiments, the occlusal portion of the teeth may be in intimate, sealing contact with the tray such that there is a lingual chamber around the teeth and a buccal chamber around the teeth with at least one port in the lingual chamber and at least one port in the buccal chamber. When vacuum is applied to one chamber then fluid from the irrigant source will be pulled around all surfaces of the teeth at the gum-line and through the interproximal spaces to the vacuum side.

Similar trays may be made for both the maxilla and mandible, and can be connected to each other for simultaneous insertion and removal. The hoses or lines may be connected to a router which is in turn connected to both an irrigant fluid supply reservoir and a vacuum pump. The router may direct either fluid or vacuum to the various hoses with the routing changing over time for optimum cleaning. The router may be under user or automatic control to determine which ports, at any given time, have either vacuum or fluid source connection.

The hose leading from the irrigant source to the tray may be constructed such that when cleaning fluid is sucked up, air can be sucked up or injected into the hose (as from another source or the atmosphere) in varying amounts, to create bubbles, water droplets, and/or boluses of the cleaning fluid to increase and focus the hydrodynamic forces of the fluid upon reaching the teeth. In practice, this has been found to be more effective at removing biofilm than consistent laminar or turbulent fluid flow alone. This combination of mechanical forces and chemotherapeutic affect may remove and/or kill the biofilm. Use on a consistent basis may resolve and prevent gingival inflammation.

The present disclosure also includes methods and processes for related to the use of such systems, as detailed further herein.

DESCRIPTION OF THE DRAWINGS

It will be appreciated by those of ordinary skill in the art that the various drawings are for illustrative purposes only. The nature of the present disclosure, as well as other embodiments, may be more clearly understood by reference to the following detailed description, to the appended claims, and to the several drawings.

DETAILED DESCRIPTION

The present disclosure is directed to systems and methods for cleaning teeth by removal of dental biofilm. It will be appreciated by those skilled in the art that the embodiments herein described, while illustrative, are not intended to so limit the scope of the appended claims. Those skilled in the art will also understand that various combinations or modifications of the embodiments presented herein can be made without departing from the scope of this disclosure. All such alternate embodiments are within the scope of the appended claims.

Figure 1A:
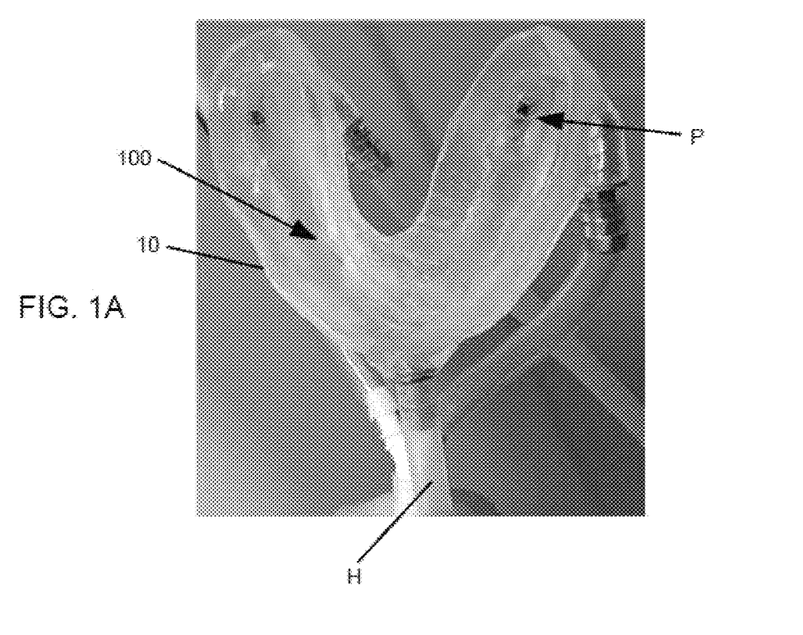
FIGS. 1A, 1B, and 1C are top, bottom, and rear perspective views of a custom irrigation tray useful with a first embodiment of the teachings of this disclosure.
Figure 1B:
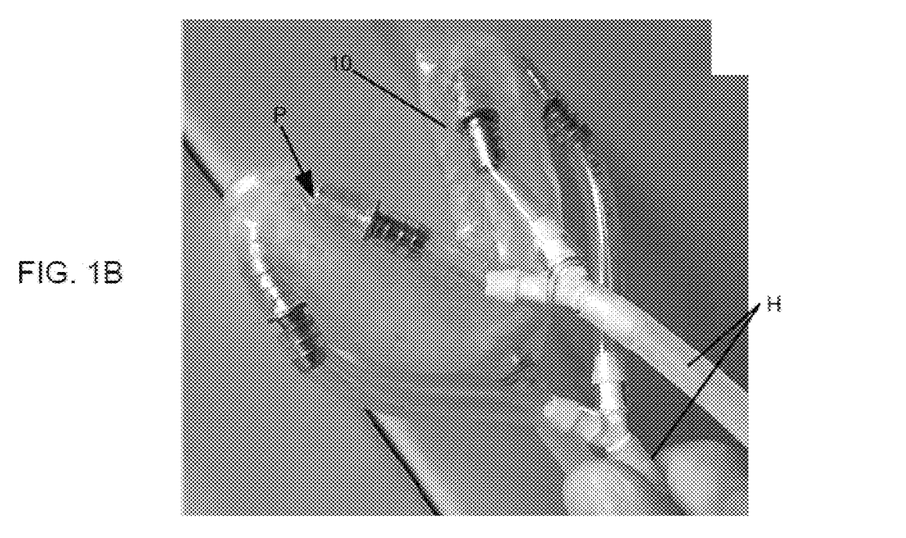
Figure 1C:
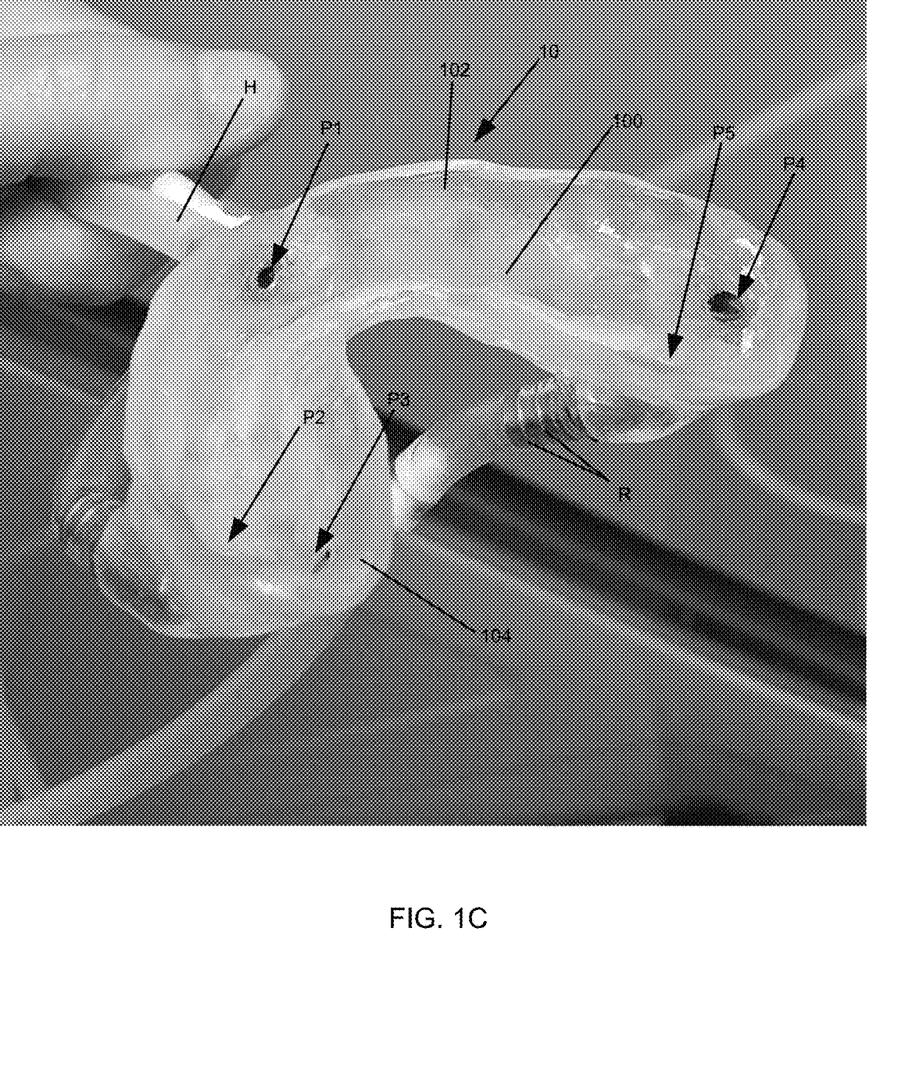

Referring to the drawing figures, depicted in FIGS. 1A, 1B, and 1C is a first embodiment of custom-fit tray 10 that fits over the teeth and seals against the gum of a mammal. It will be appreciated that the depicted tray 10 is for maxillary use, and a single tray for mandibular use may be constructed in a similar fashion but used in the opposite orientation.

A number of ports P are embedded in the tray, each in fluid communication with a hose or line H. As explained below, during use the hoses H are supplied with either vacuum or an irrigant/fluid source. Upon installation, there is a small space between the tray and the teeth that provides for fluid to flow around the teeth.

Figure 2A:
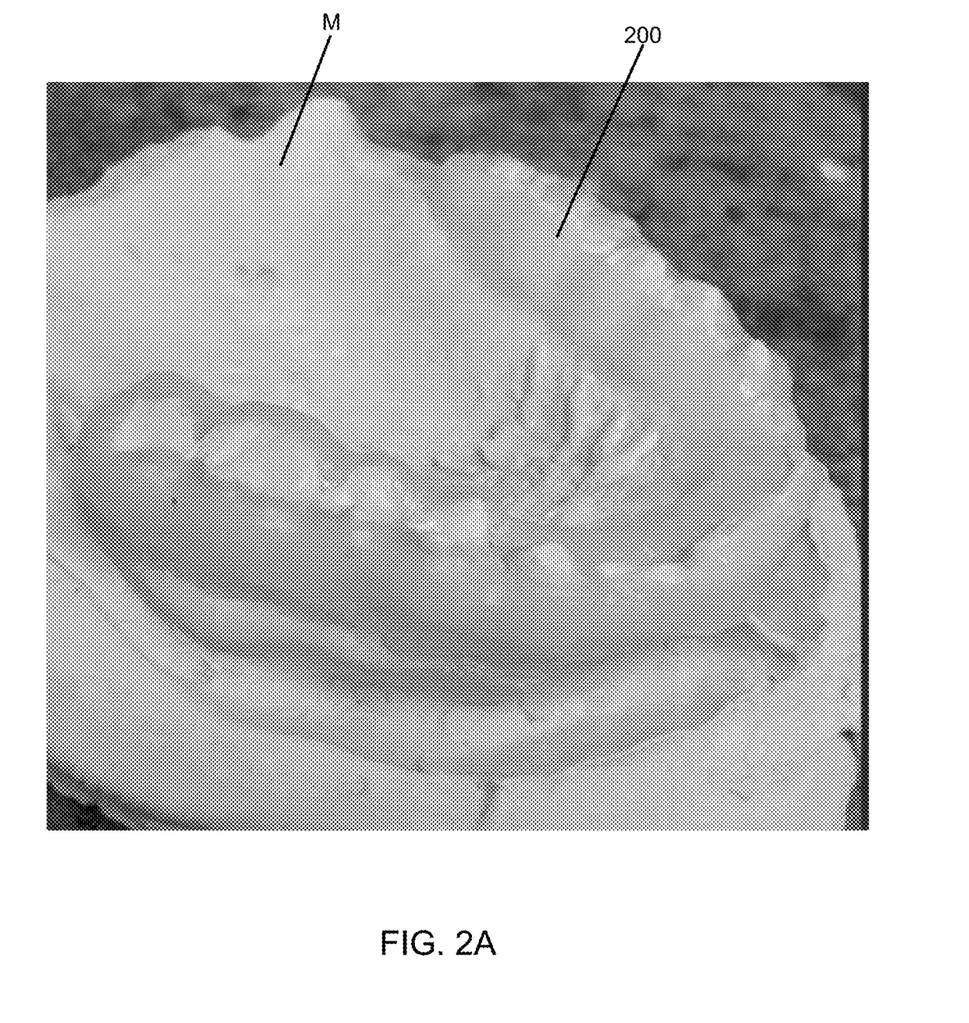
FIG. 2A is a perspective view of a portion of a model of a patient's teeth and gums with a spacer for the manufacture of the irrigation tray of FIGS. 1A, 1B and 1C.

For use with a system, each tray 10 may be custom-made with a very precise fit for each patient. In some embodiments, this may be done for the patient (who can be any mammal) by taking a mold (or scan) of the patient's maxilla and mandible and then making a model, similar to model M depicted in FIGS. 2A and 2B, using methods known to those of skill in the art. Model M may be constructed of plaster, a thermoplastic material or other suitable materials.

Using the model M, a sheet of desired material may be vacuum formed on the model. In the depicted embodiment, the sheet may be an EVA (ethylene vinyl acetate) monolayer sheet to form tray 10. It will be appreciated that other sheets constructed from suitable materials may be used.

Prior to application of the sheet, the region of the model M corresponding to the patient's gum tissue may be lightly air abraded to allow a tighter fit of the tray to the gum tissue. One or more spacers 200 may be placed on the portion of the mold M corresponding to the patient's teeth such that the final end user tray 10 will have a relatively uniform clearance/recess/space of a desired distance around all surfaces of all teeth in relation to the tray 10 interior intaglio surface 100. In some embodiments, this flow space may be from about 1 mm to about 2 mm to allow for proper fluid flow. Additionally, the fluid flow may extend up to, but not go past, the gingival margin depicted at GM in FIG. 2B.

In the depicted embodiment, the spacer 200 extends from the occlusal surface just to the gingival margin. The spacer 200 may be constructed from a wax having a melting point higher than the temperature required for the sheet overlay and vacuum seal, modeling clay, or another suitable substance may be used. This portion of the patient's oral cavity enclosed by the sheet defines the area intended to be irrigated by systems in accordance with the present disclosure, and typically contains the patient's exposed tooth surface. By excluding the majority of the gums and the rest of the oral cavity from irrigation, fluid flow is directed at the intended area and patient comfort (and thus compliance) may be increased.

Figure 2B:
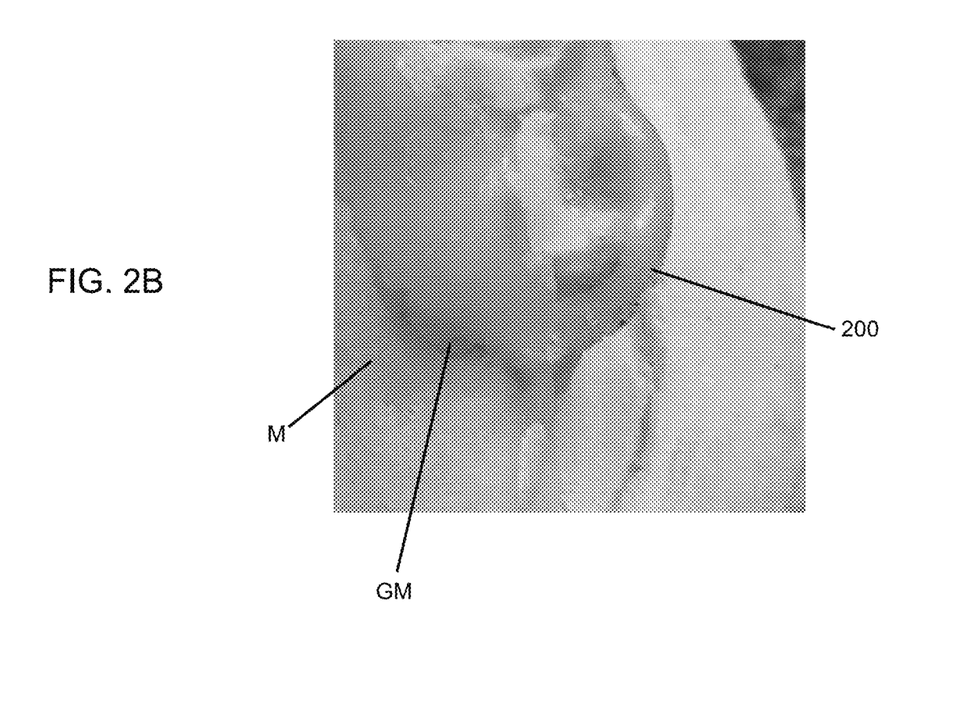
FIG. 2B is a close up view of a portion of FIG. 2A.

The portion of the model M corresponding to the patient's occlusal surfaces may be left bare of spacers so that upon application of the vacuum, the sheet will "suck-down" and engage the occlusal portion of the teeth and make a seal as shown FIG. 2B. The distal aspects of the molars and tooth surfaces adjacent to any edentulous spaces, from a point about 3 mm coronal to the marginal gingiva, will similarly not have block out material which will allow the sheet to conform to these tooth surfaces. This will prevent free fluid flow from buccal chamber to lingual chamber during use. Thus, during use, the cleaning fluid will be forced to flow: 1) interproximally, 2) in close proximity to the gingival margins of the distal aspects of terminal molars and 3) in teeth bounding edentulous spaces. In embodiments for certain patients, this may be varied, as by lacking an occlusal block during sheet forming so the final tray lacks two separate distinct spaces between buccal and lingual. Such variations may be determined by a dental practitioner as appropriate for an individual patient.

In some alternative embodiments, a tray 10 may be made from a sheet which is a prefabricated laminate material with an exterior that is semi-rigid and an interior that is a rubberized material (such as material currently being used for vacuum formed mouth guards). In other embodiments, the tray 10 could be constructed by three dimensional printing from a CAD/CAM file, by Injection molding, or by building up a tray by passive addition of material to the mold M.

Upon or during forming of the tray 10, a number of ports P will be either molded in or inserted into the tray 10. In the depicted embodiments, there are five ports P, one P1 placed in the front wall 102 of the tray 10, and two near each distal end of the tray 10, one placed through each of the front wall 102 and rear wall 104, designated P2, P4, and P3, P5, respectively.

The port P may be metal and have a connection end for attachment to a hose H. In the depicted embodiment, the connection end includes a series of ridges R around the outer surface of the hollow bore for retaining a hose H end upon insertion. Where metal ports P are used, these may be placed in the tray 10 by being heated and inserted through the tray 10 material after vacuum forming. Where the material is EVA, additional EVA may then be heated and added around the ports for sealing and to provide structural reinforcement of the surrounding EVA. For other materials, suitable sealing and reinforcement may be used.

It will be appreciated that in other embodiments, the ports may be placed in other fashions. For example, where the tray 10 is formed by injection molding, the ports P may be placed or embedded in an injection mold to allow the injected material to flow around the ports and retain them. Where the tray 10 is formed by passive material application on a mold M, the ports may be luted in place or added afterward by drilling holes in the tray and luting the ports in. In other embodiments, the ports P may be continuous with a connected hose H and formed by embedding hoses into the tray.

In some embodiments, a removable sleeve may be needed in manufacturing, or left in permanently, inside the tube lumen where the hose H joins the tray to keep the hose from collapsing or kinking. This may be removed post manufacture. In some embodiments a metal sleeve having a diameter slightly smaller than the diameter of the hose H may be used.

The tray 10 may have baffles, blocks, barriers or other flow directors on the intaglio surface that would direct turbulent flow of irrigant past all tooth surfaces where needed to prevent any fixed, low velocity eddies. This may vary from tray to tray as needed for customization to a particular patient.

In some embodiments, the tray 10 may be formed so the occlusal portion of the teeth may be in intimate, sealing contact with the tray 10 such that there is a lingual chamber around the teeth and a buccal chamber around the teeth with at least one port P in the lingual chamber and at least one port P in the buccal chamber. In use, when vacuum is applied to one chamber then fluid from the irrigant source will be pulled around all surfaces of the teeth at the gum-line and through the interproximal spaces to the vacuum side.

Figure 3:
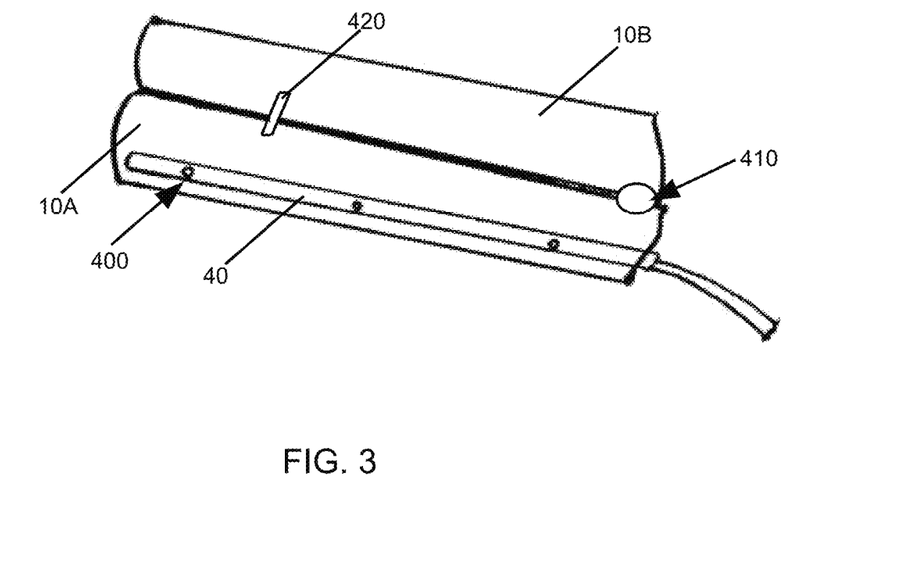
FIG. 3 is a side view of a second embodiment of custom irrigation trays useful with another embodiment of the teachings of this disclosure.

Turning to FIG. 3, in some embodiments, a tray 10A may include a vacuum hose 40 which has one or more vacuum ports 400, which may be formed as perforations, disposed on an exterior surface of the tray 10A. In use, the vacuum hose is connected through a connection port to a constant vacuum. The saliva produced in a patient's mouth during a treatment session is then evacuated through the vacuum hose 40. This provides increased comfort for the patient by preventing the buildup of saliva and drooling during treatment.

As also depicted in FIG. 3, in some embodiments, two customized trays, 10A and 10B may be joined together to allow both the maxilla and mandible to be treated at the same time. These trays 10A and 10B may be connected to each other for simultaneous insertion and removal, as depicted. Where the trays 10A and 10B are connected, they may be bonded together along at least a portion of their lengths, with a breather hole 410 formed between the two in the anterior region such that the patient can mouth breath if necessary.

The connected trays may be individually manufactured for each of the mandible and maxilla as discussed previously herein. After each tray is individually formed, they may be connected by mounting each tray on its respective model of the patient's teeth. By using an articulator on which the models may be mounted and a bite index obtained from the patient, the trays 10A and 10B may then be connected to one another in an anatomically correct pre-indexed relationship. Then, during use, when a patient bites into the trays, the upper tray 10B and lower tray 10A are seated correctly/uniformly on the teeth. One or more communication tubes 420 between the upper and lower trays 10B and 10A may allow fluid flow between the two during operations.

For use, each port P may be connected (singly or in groups) to a hose H. The hoses H may in turn be connected to a source of irrigant for irrigating the teeth or to a vacuum source, such as a vacuum pump, for removal of irrigant from the tray 10. The hose H leading from the irrigant source to the tray 10 may be constructed such that when cleaning fluid is sucked up, air can be sucked up or injected into the hose H (as from another source or the atmosphere) in varying amounts, to create bubbles, water droplets, and/or boluses of the irrigant cleaning fluid to increase and focus the hydrodynamic forces of the fluid upon reaching the teeth. In practice, this has been found to be more effective at removing biofilm than consistent laminar or turbulent fluid flow alone. This combination of mechanical forces and chemotherapeutic affect may remove and/or kill the biofilm. Use on a consistent basis may resolve and prevent gingival inflammation.

Figure 4A:
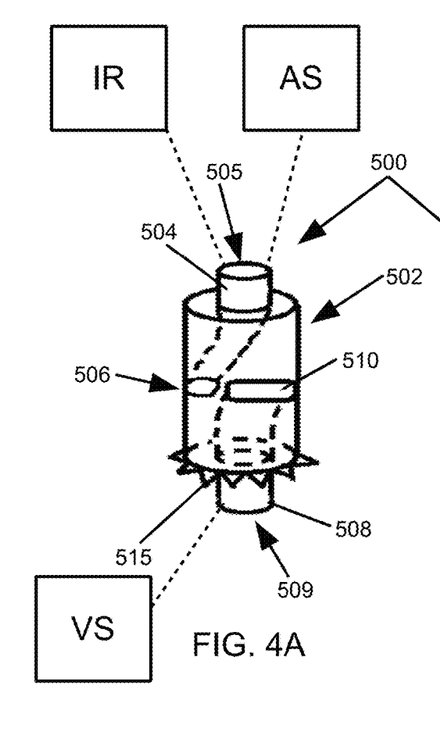
FIG. 4A is a side perspective view of a rotating piston for a router valve useful with some embodiments of systems in accordance with the present disclosure.
Figure 4B:
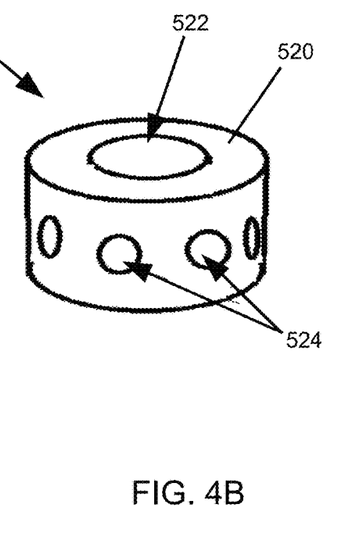
FIG. 4B is a perspective side view of a valve body for use with the rotating piston of FIG. 4A.

Turning to FIGS. 4A and 4B, the hoses H connected to the ports P or lines may be connected to a router 500 which is in turn connected to both an irrigant fluid supply reservoir and a vacuum pump. The router 500 may direct either fluid or vacuum to the various hoses H with the routing changing over time for optimum cleaning. The router 500 may be under user or automatic control to determine which ports P, at any given time, have either vacuum or fluid source connection.

As depicted, one embodiment of a suitable router 500 may include an inner rotating valve piston 502 and an outer valve ring 520. The valve piston 502 may include a body formed as a cylinder with a first intake tube 504 extending from a first end of the body to a distal opening 505. The intake tube 504 then passes through the body to one or more exit ports 506 positioned at a side surface of the body. A suction tube 508 extends from the second end of the body to a distal opening 509. The suction tube 508 then passes through the body to one or more suction ports 510 positioned at a side surface of the body. A set of teeth 515 to serve as a drive gear may be positioned around the body as well, for example around a lower edge.

It will be appreciated that the suction tube 508 may branch as it passes through the piston body to more than one suction port 510. This may allow for additional use of ports P to remove fluid from the tray 10 during use at the same time. This can amplify both the flow through into the tray the ports P then in use for fluid supply, and increase the hydrodynamic forces in the tray as well.

The outer valve ring 520 may be formed as a body having a central bore 522 in which the body of the rotating piston 502 may be positioned. A series of hose H connection ports 524 are disposed around the body of the ring 520 passing therethrough to the central bore 522.

In use, hoses H connect the hose connection ports 524 to the ports P on a tray 10. Suction tube 508 is connected to a vacuum source (depicted schematically as VS) and intake tube 504 is connected to an irrigant reservoir (depicted schematically as IR). The piston 502 is rotated in the ring 520, as by drive of the teeth 515. During rotation, the exit ports 506 and suction ports 510 pass into and out of alignment with the connection ports 524. Each hose H and associated port P on tray is thus both used to inject irrigant flow into the tray 10 and to pull irrigant for removal from the tray 10 as the piston 502 is rotated.

Importantly, the router can provide for differentiated flow patterns. For example, in a tray 10 having five ports P, the number of ports being used for injection versus suction can be rotated from 1 to 4 each in various numbers and conformations as treatment is conducted. This allows for multiple flow patterns within the tray 10 to be created in order to facilitate cleaning.

It will be appreciated that the ratio of supply to vacuum ports currently in use at a given time may be dependent on the number and/or volume of suction ports 510 in comparison to exit ports 506. As an example, if the exit ports 506 are the same diameter as hose connection ports 524, then each exit port 506 would effectively "drive" one port P in the tray with supply. At the same time, if the suction port 510 was large enough to encompass multiple connection ports 524, this would result in multiple ports P per tray 10 being under vacuum. In this example, the tray 10 (and lone supply port P) would experience four times the vacuum force as compared to a 1:1 relationship of vacuum ports to supply ports (i.e. as compared to a scenario where vacuum port 510 was connected to only one port P). This increased vacuum to the tray (as compared to supply) would translate into increases hydrodynamic force from the single supply connected port P in the tray which may remove more biofilm on the teeth being sprayed as compared to a scenario where there is a 1:1 relationship of supply ports to vacuum ports.

For use, a tray 10 is positioned in a patient's mouth, positioned over the teeth and contacting and sealing against the gum tissues. Where a dual tray embodiment such as that depicted in FIG. 3 is used, both the upper and lower teeth are covered for simultaneous treatment. It will be appreciated that embodiments where only a partial seal against the gum tissues is achieved may be used provided that the seal is sufficient to provide for the requisite flow and fluid dynamics, with only a minor amount of fluid leaking from the tray into the patient's mouth or a minor loss of the applied vacuum that does not significantly reduce the hydrodynamic forces at the ports P. This may be especially useful where a patient has a unique oral topography, as may be caused by past tooth loss or disease.

A cleaning cycle is then commenced with one or more cleaning irrigant fluid(s) circulated through tray 10 and around and between the teeth. The fluid(s) are supplied through one or more port(s) P and vacuum is applied to one or more port(s) P to create the fluid flow. The cycle parameters, including fluids and time may be controlled by a user by directly adjusting the hose H connections, or may be performed by an "automatic" system using a control circuit to provide a preprogrammed cycle.

Typical cleaning sessions may be from about 1 to about 15 minutes in duration. These may vary on the setting (home vs. clinician's office), cleaning fluids used, and particulars of the cleaning protocol.

In one illustrative embodiment of a daily home use, a first cleaning fluid comprising a solution for softening or removal of dental biofilm, followed by the circulation of a second cleaning fluid comprising a solution for disinfection by killing microorganisms, including bacteria. Typical times may be about 5 minutes for the first solution and about three minutes for the second solution. The first solution may be urea/dodecyl sulfate combination and the second a hypochlorite solution, which may be about 0.7%. A third solution for additional cleansing, such as a 1:100 povidone iodine, could be used for a third cleansing cycle It will be appreciated that where multiple fluids are used, that multiple reservoirs for containing such fluids may be used. Typically, such fluids will be discarded after use and the system may be configured to flow the used fluids into a sink for draining, meaning that only fluids acceptable for disposal in residential sewage systems may be acceptable for home use.

It will be appreciated that any suitable cleaning irrigant solutions useful for a particular application may be used. Non-limiting examples include NaOCl solutions, HOCl solutions, chlorhexidine solutions, povidone-iodine solutions, water, ozonated water, salt water, urea solutions, urea/surfactant solutions, slurry of water/NaHCO3, and other water/abrasive slurries that are biocompatible. The use of slurries can provide hydrodynamic (mechanical) removal of dental biofilm. Suitable slurries may include a suitable abrasive, such as pumice or granular sodium bicarbonate, suspended in a fluid. Solutions that achieve hydrodynamic removal in combination with chemical removal and killing of pathogens may be especially useful. For example, a focused jet of NaOCl may be used to both remove biofilm remove and kill bacteria.

For home use, a cleaning cycle may be performed by a patient on a regular basis. For example, short cycles may be performed daily, or twice a day. Alternatively, it could be done on a periodic basis, such as every other day, or weekly, as an adjunct to brushing and flossing. One example may be the use of a povidone-iodine solution once a week with a dual urea/dodecyl sulfate solution followed by a hypochlorite solution cycle. Cycles and parameters may be adjusted as determined by clinical studies and particular patient response.

Where a tray 10 includes at least one P port on the "lingual" (tongue side) and at least one port P on the "facial" or lip side, they may be used to provide suction and supply to pull the solution in between the teeth which is the most difficult place to get clean (hence the need for floss). In one illustrative embodiment, there would be a port on each of the lingual and facial sides for each tooth interproximal space (space between teeth) which would provide a supply and vacuum for each space between teeth.

As a cleaning cycle is performed, at least one hydrodynamic parameter of the fluid flow in the tray may be altered by the addition of air into the incoming first cleaning solution. For example, air may be injected into the hose H (as from a compressed air source, depicted schematically as AS in FIG. 4A, or obtained from the atmosphere by the system) in varying amounts, to create bubbles, water droplets, and/or boluses of the irrigant cleaning fluid as it exits the port P into the tray 10. This will increase and focus the hydrodynamic forces of the fluid upon reaching the teeth. In practice, this has been found to be more effective at removing biofilm than consistent laminar or turbulent fluid flow alone. This combination of mechanical forces and chemotherapeutic affect may remove and/or kill the biofilm. Use on a consistent basis may resolve and prevent gingival inflammation. Where an automated system is used, the injection of air may be controlled by a controller following a preprogrammed protocol.

Vacuum force amplification may similarly be used to increase and alter the hydrodynamic forces during a cleaning cycle. For example, the ports P may be used for both irrigant injection and vacuum removal at different points of the cleaning cycle. Where multiple ports P are present in the tray 10, the individual ports may be rotated through use as an injection port or as a vacuum port. This may be performed using a router similar to router 500 discussed previously herein to achieve differentiated flow patterns. For example, in a tray 10 having ten or twenty ports P, the number of ports being used for injection versus suction can be rotated from one to nine or nineteen each in various numbers and conformations as treatment is conducted. This allows for multiple flow patterns within the tray 10 to be created in order to facilitate cleaning. Additionally, it allows for changes in the fluid supply velocity by amplifying or reducing the amount of fluid flowing through the tray 10 as more or fewer ports are used for evacuation or supply.

In practice, two locations in a tray 10 where fluid velocity can be measured include: 1) at any particular port P (either for irrigant supply flowing therethrough into the tray 10 or for irrigant removal by vacuum therethrough from the tray 10) during treatment, and 2) a general flow measurement throughout the tray which could be measured (as a proxy) at the confluence of the connection of all vacuum ports close to the vacuum source. The velocity at both of these points is important, different, and (depending on the ratio of irrigant/vacuum ports) inversely proportional. In one example, using a tray 10 having ten ports P, parameters that maximize irrigant hydrodynamic force at any particular port P (i.e., where 9 ports P are used to apply vacuum and 1 port P to supply irrigant) this will likely decrease general fluid flow through the tray, while the 5 port supply to port vacuum configuration would likely maximize irrigant flow generally through the entire tray, but minimize the hydrodynamic force at any one of the 5 irrigant supply ports. In addition, the opposite extreme (1 port P applying vacuum and 9 port P supplying irrigant) would have utility as well for low flow rates of costly, but highly effective irrigants. Given particular treatment regimens and individual patient needs, a particular treatment may need to maximize or minimize fluid flow throughout the tray, and/or maximize or minimize the hydrodynamic force at a particular port P.

While this disclosure has been described using certain embodiments, it will be appreciated that the teachings herein may be further modified within the spirit and scope of this disclosure. This application is therefore intended to cover any variations, uses, or adaptations of this disclosure which use its general principles. Further, this application is intended to cover such departures from the present disclosure as come within known or customary practices in the art to which this disclosure pertains and which fall within the limits of the appended claims.

What is claimed is:

1. A method of cleaning a patient's teeth, the method comprising:

placing at least a first tray having a front wall and a rear wall for enclosing a set of teeth of a patient and a plurality of ports through the tray into a patient's mouth, such that the front wall and rear wall at least partially seal against the patient's gum tissue to create an enclosed flow space around the teeth;

applying a vacuum to at least one of the plurality of ports to draw a cleaning solution through at least a second of the plurality of ports to create a flow of a first cleaning solution through the tray and thereby cleaning the patient's teeth; and altering at least one hydrodynamic parameter of the flow of the first cleaning solution in the tray by the addition of air into the incoming first cleaning solution by introducing air into a hose carrying the first cleaning solution to the tray.

2. The method according to claim 1, wherein altering at least one hydrodynamic parameter of the flow of the first cleaning solution in the tray by the addition of air by introducing air into a hose carrying the first cleaning solution to the tray comprises injecting air into a hose carrying the first cleaning solution to the tray.

3. The method according to claim 2, wherein injecting air into a hose carrying the first cleaning solution to the tray comprises injecting air into the hose from a compressed air source.

4. The method according to claim 1, wherein altering at least one hydrodynamic parameter of the flow of the first cleaning solution in the tray by the addition of air comprises creating air bubbles in the first cleaning solution, introducing the first cleaning solution to the tray as a series of boluses, introducing the first cleaning solution to the tray as droplets in an air flow, or a combination thereof.

5. The method according to claim 1, further comprising switching each port of the plurality of ports from applying vacuum to the tray to supplying the first cleaning solution to the tray on an individual basis to create different flow patterns in the tray.

6. The method according to claim 1, further comprising switching individual ports of the plurality of ports from supplying the first cleaning solution to the tray to applying vacuum to the tray to vary fluid flow velocity in the tray and increase hydrodynamic forces at cleaning solution supplying ports by utilizing differing numbers of ports for fluid removal and supply.

7. The method according to claim 1, wherein the method further comprises ceasing the flow of the first cleaning solution through the tray after a duration and then creating the flow of a second cleaning solution through the tray.

8. The method according to claim 7, wherein the flow of the first cleaning solution softens dental biofilm and the flow of the second cleaning solution removes dental biofilm.

9. The method according to claim 1, wherein the first cleaning solution is selected from the group comprising NaOCl solutions, HOCl solutions, chlorhexidine solutions, povidone-iodine solutions, water, ozonated water, salt water, and urea solutions.

10. The method according to claim 1, wherein the first cleaning solution comprises a slurry to mechanically clean the patient's teeth.

11. The method according to claim 1, wherein placing at least a first tray having a front wall and a rear wall for enclosing a set of teeth of a patient and a plurality of ports through the tray into a patient's mouth, such that the front wall and rear wall at least partially seal against the patient's gum tissue to create an enclosed flow space around the teeth comprises inserting at least a first tray connected to an at least a second tray to enclose both the upper and lower teeth of the patient for simultaneous treatment, wherein the at least a first tray and at least a second tray are in an anatomically correct pre-indexed relationship to one another for the patient.

12. The method of claim 1 further comprising, applying suction to a line disposed around an outside edge of the at least a first tray to remove saliva produced by the patient during treatment from the patient's mouth via suction ports in the line.

13. A method of cleaning a patient's teeth, the method comprising:

placing at least a first tray having a front wall and a rear wall for enclosing a set of teeth of a patient and a plurality of ports through the tray into a patient's mouth, such that the front wall and rear wall seal against the patient's gum tissue to create an enclosed flow space around the teeth;

applying a vacuum to at least one of the plurality of ports to draw a cleaning solution through at least a second of the plurality of ports to create a flow of a cleaning solution through the tray and thereby cleaning the patient's teeth; and varying flow velocity of the cleaning solution in the tray by switching each port of the plurality of ports from applying vacuum to the tray to supplying the first cleaning solution to the tray on an individual basis to utilize differing numbers of ports for fluid removal from the tray.

14. The method according to claim 13, wherein varying flow velocity of the cleaning solution in the tray by switching each port of the plurality of ports from applying vacuum to the tray to supplying the first cleaning solution to the tray on an individual basis to utilize differing numbers of ports for fluid removal from the tray further comprises rotating the application of vacuum between ports to produce varied flow patterns by varying the positions of the ports which are drawing cleaning solution from the tray.

15. The method according to claim 14, wherein rotating the application of vacuum between ports to produce varied flow patterns by varying the positions of the ports which are drawing cleaning solution from the tray comprises actuating a router valve which is in fluid communication with the plurality of ports in the tray and in fluid communication with both a source of a cleaning fluid and a vacuum source that is in fluid communication with a least one port disposed in the at least a first tray and in fluid communication with a first port disposed on the router valve.

16. The method according to claim 15, wherein actuating a router valve comprises rotating a rotary piston in a valve body.

17. The method according to claim 13, wherein the cleaning solution is selected from the group comprising NaOCl solutions, HOCl solutions, chlorhexidine solutions, povidone-iodine solutions, water, ozonated water, salt water, and urea solutions.

18. The method according to claim 13, wherein the cleaning solution comprises a slurry to mechanically clean the patient's teeth.

19. The method according to claim 13, wherein placing at least a first tray having a front wall and a rear wall for enclosing a set of teeth of a patient and a plurality of ports through the tray into a patient's mouth, such that the front wall and rear wall seal against the patient's gum tissue to create an enclosed flow space around the teeth comprises inserting at least a first tray connected to an at least a second tray to enclose both the upper and lower teeth of the patient for simultaneous treatment.

20. The method according to claim 19, wherein the at least a first tray and at least a second tray are in an anatomically correct pre-indexed relationship to one another for the patient.

21. The method according to claim 13, further comprising applying suction to a line disposed around an outside edge of the at least a first tray to remove saliva produced by the patient during treatment from the patient's mouth via suction ports in the line.

* * * * *